United States Patent
Aoki et al.

(10) Patent No.: US 6,379,887 B1
(45) Date of Patent: Apr. 30, 2002

(54) GENE FOR INHIBITING MELANIN BIOSYNTHESIS

(75) Inventors: Hirofumi Aoki; Ohji Ifuku, both of Kanagawa-ken (JP); Antonis S. Zervos, Charlestown, MA (US)

(73) Assignees: The General Hospital Corporation, Boston, MA (US); Shiseido Company, Ltd., Tokyo (JP)

(*) Notice: Subject to any disclaimer, the term of this patent is extended or adjusted under 35 U.S.C. 154(b) by 0 days.

(21) Appl. No.: 09/150,766

(22) Filed: Sep. 10, 1998

(51) Int. Cl.$^7$ .......................... C12Q 1/68; C12P 19/34; C07H 21/04; C07K 5/00
(52) U.S. Cl. .................... 435/6; 435/91.2; 536/23.1; 536/24.33; 530/300
(58) Field of Search .................. 536/23.1, 24.33; 435/6, 91.1, 91.2; 530/300

(56) References Cited

PUBLICATIONS

Colin A. Hodgkinson, et al., "Mutations at the Mouse Microphthalmia Locus Are Associated with Defects in a Gene Encoding a Novel Basic–Helix–Loop–Helix–Zipper Protein", *Cell*, Jul. 30, 1993, vol. 74, pp. 395–404.
Michael J. Hughes, et al., "A Helix–Loop–Helix Transcription Factor–like Gene Is Located at the mi Locus*", *The Journal of Biological Chemistry*, Oct. 5, 1993, vol. 268, No. 28, pp. 20687–20690.
Masayoshi Tachibana, et al, Cloning of MITF, the human homolog of the mouse *microphthalmia* gene and assignment to chromosome 3p14.1–p12.3, *Human Molecular Genetics*, 1994, vol. 3, No. 4, pp. 553–557.
Ken–ichi Yasumoto, et al., "Microphthalmia–Associated Transcription Factor as a Regulator for Melanocyte–Specific Transcription of the Human Tyrosinase Gene", *Molecular and Cellular Biology*, Dec., 1994, vol. 14, No. 12, pp. 8058–8070.
N.J. Bentley, et al., "Melanocyte–Specific Expression of the Human Tyrosinase Promoter: Activation by the Microphthalmia Gene Product and Role of the Initiator", *Molecular and Cellular Biology*, Dec., 1994, vol. 14, No. 12, pp. 7996–8006.

Ruth Ganss, et al., "The Mouse Tyrosinase Gene", *The Journal of Biological Chemistry*, Nov. 25, 1994, vol. 269, No. 47, pp. 29808–29816.
Timothy J. Hemesath, et al., "*microphthalmia*, a critical factor in malanocyte development, defines a discrete transcription factor family", *Genes & Development*, 1994, pp. 8:2770–2780.
Karen J. Moore, "Insight into the *microphthalmia* gene", *Trend in Genetic*, Nov. 1995, vol. 11, No. 11, p442–p448.
Rainer Pepperkok, et al., "Casein Kinase II Is Required for Transition of $G_0/G_1$, Early $G_1$, and $G_1/S$ Phases of the Cell Cycle*", *The Journal of Biological Chemistry*, Mar. 4, 1994, vol. 269, No. 9, pp. 6986–6991.
Uwe Pott, et al., "A New $Cys_2/His_2$ Zinc Finger Gene, rKr2, Is Expressed in Differentiated Rat Oligodendrocytes and Encodes a Protein with a Functional Repressor Domain", *Journal of Neurochemistry*, 1995, vol. 65, No. 5, pp. 1955–1966.
XVIth International Pigment Cell Conference, Oct. 29–Nov. 3, 1996.
7th Meeting of the PanAmerican Society for Pigment Cell Research, Jun. 15–Jun. 18, 1997.
XIIth Annual Scientific Meeting of the Japanese Society for Pigment Cell Research, Dec. 6–Dec. 7, 1997.
Levitan, Max Textbook of Human Genetics, 3rd ed. Oxford University Press, pp 32–35, 1988.*
SHlesinger, D.H. (ed) Macromolecular Sequencing and Synthesis Selected Methods and Applications, pp. 127–149, 1988.*
Genbank—est107, accession No. AA123106, Nov. 1996.*
Steingrimsson et al. The EMBO Journal, vol. 15, pp. 6280–6289, 1996.*

* cited by examiner

*Primary Examiner*—W. Gary Jones
*Assistant Examiner*—Jehanne Souaya
(74) *Attorney, Agent, or Firm*—Wenderoth, Lind & Ponack, L.L.P.

(57) ABSTRACT

The specification relates to a gene which is involved in the control of melanin production in human melanocytes. Human homologs of rat rKr2 gene and their fragments, and a method for evaluating melanin production ability in human melanocytes using such fragments are also disclosed. These subject matters are useful mainly in the cosmetic and dermatological fields.

15 Claims, 5 Drawing Sheets

FIG. 1

```
        TCAGGGCTTAGTGCTCACCGGAGAGTCCACACGGGAGAGAAACCCTATGAGTGCAAGG
        ********** ************* ****************** ******* ****  *
2161"   ATTCAGGGCTTACTGCTCACCGGAGGGTCCACACGGGAGAGAAGCCCTATGAATGCACAG

ACTGTNGGAAAGGCTTCAGTCTTNCCTCAAGTCTACGGACTCATCAGAGAGTTCACACTG
        * *** ********** ****** ************* ********* ** ******* *
2221"   AGTGTGGGAAAGGCTTTAGTCTTGCCTCAAGTCTACGAACTCATCAGCGAATTCACACCG

GTGAGAAGCCCTTCCAATGCAATGAGTGCCAGAAGCGGTTCAGTCAGGTCTCACACCTCC
        * *****  ************************** ***********************
2281"   GCGAGAAACCCTTCCAATGCAATGAGTGCCAGAAGAGGTTCAGTCAGGTCTCACACCTCC

AGTCCCACCAGAGAGTGCACACTGGGGAGAAGCCCTACAAATGTGACCGGTGTGGGAAAG
        ************ ** ***** *********** ************  ******* *
2341"   AGTCCCACCAGAGGGTTCACACAGGGGAGAAGCCTTACAAATGTGACACCTGTGGGAAGG

CTTTCAGCCAGAAGTCTGGGCTCCAAGTC
        * ***** ** ******** *********
2401"   CCTTCAGTCAAAAGTCTGGTCTCCAAGTC
```

F I G. 4
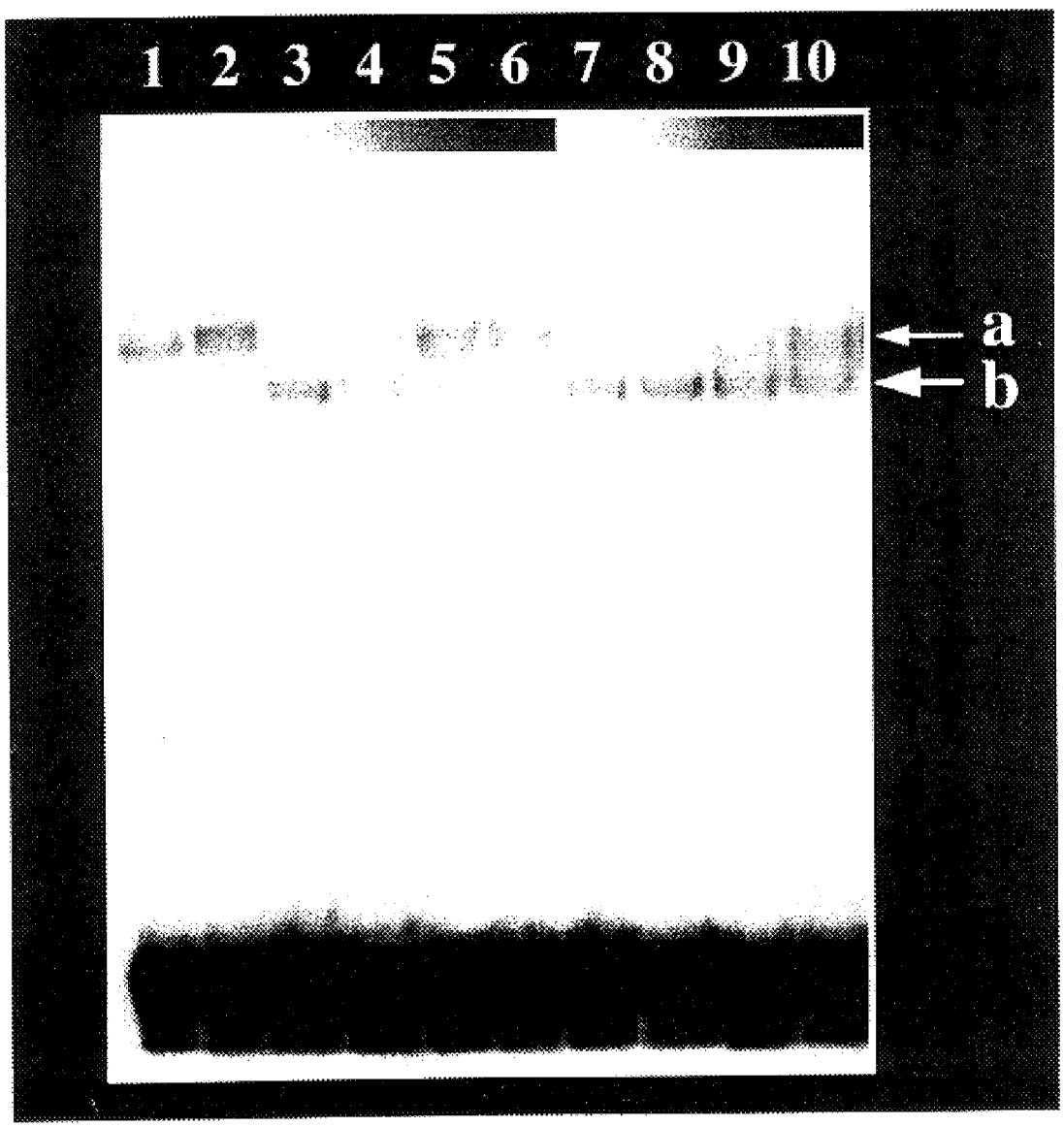

US 6,379,887 B1

GENE FOR INHIBITING MELANIN BIOSYNTHESIS

BACKGROUND OF THE INVENTION

1. Field of the Invention

This invention relates to an isolated DNA comprising a gene and a method of using the DNA. More specifically, this invention relates to a gene encoding a protein inhibiting the action of human microphthalmia-associated transcription factor (MITF) and the expression of the gene, and a method for evaluating the ability of human melanocytes to express the above protein, using a DNA fragment from the gene.

2. Description of the Related Art

The microphthalmia gene (mi) of mice is known, based on their mutant strains lacking the gene, to be involved in phenotypes such as the loss of pigmentation, small eyes, the defection of mast cells and abnormality in bones. This gene is located on chromosome No. 6. Since the absence of the mi gene results in abnormalities in different areas, it is suggested that the gene is involved in various controls in the embryological stage.

This mouse mi gene was recently cloned. As a result of analyses of the gene, it was found that the gene encodes a transcription factor protein having a basic-helix-loop-helix-zipper structure (hereinafter referred to as "b-HLH-ZIP structure") which is known to be involved in protein-protein interactions (Hodgkinson, C. A. et al., Cell, 74, 395–404 (1993); Hughes, M. J. et al., J. Biol. Chem., 268, 20687–20690 (1993)). Thereafter, a human mi gene (hereinafter referred to as "mitf") which is homologous to the mouse mi gene, was also cloned, and was found to be located on chromosome No. 3 (Tachibana, M. et al., Hum. Mol. Genet., 3, 553–557 (1994); Yasumoto, K. et al., Mol. Cell. Biol., 14, 8058–8070 (1994)).

Incidentally, it is known that the cell-specific expression of a tyrosinase gene is controlled by several positive and negative elements existing in the promoter region. It was suggested that the expression of the gene of human tyrosinase is controlled by four positive elements and one negative element, and when the MITF as the product of a human mitf gene is bound to two E-box motifs (CATGTG) contained on the promoter region of the tyrosinase gene, the promoter activity of the tyrosinase gene is heightened (Bentley, N. J., et al., Mol. Cell. Biol., 14, 7996–8006 (1994)). Likewise, it is also reported that in mice, when the Mi as the product of a mouse mi gene is bound to a M-box (a motif conserved by the promoters of tyrosinase, TRP-1 and TRP-2) as one of the positive elements, the promoter activity of the tyrosinase gene is heightened (Ganss, R., et al., J. Biol. Chem., 269, 29808–29816 (1994)).

Further, it has been clarified that mouse Mi protein forms a family as a homodimer or a heterodimer with TFEB, TFE3 or TFEC (each thereof is b-HLH-ZIPmi) and binds to DNAs (Hemesath, T. J. et al., Gene & Dev., 8, 2770–2780 (1994)).

Under these findings, the present inventors began searching for proteins which interact with human MITF as a target molecule. The inventors believed that if proteins which can interact with human MITF and act inhibitorily thereon, could be identified, each of the molecules could be expected to inhibit melanin formation in mammal cells at an initial stage. Such substances involved in the melanin formation system have a possibility, for example, to serve as agents for controlling whitening or tanning in the cosmetic and dermatological field from the viewpoint of, so-called, pigment cell biology.

Heretofore, as substances having whitening action, there have been, for example, mentioned tyrosinase inhibitors, endothelin inhibitors, reducing agents of melanin intermediate products, etc. However, these substances either inhibit partial melanin synthesis stimulation input, or, under some circumstances, reduce or inhibit the production of melanin which are continuously formed at the site of melanin deposition, etc. Therefore, these substances are not sufficient since they do not stop the causes of melanin deposition, etc. As a result, compounding substances having whitening action which control basic melanin synthesis are sought to overcome the problems of prior art substances.

Namely, if a protein interacting with human MITF as a target molecule and a gene encoding it exist, and the protein can inhibit the action of human MITF, they will serve as a control of the basic pigment synthesis system.

SUMMARY OF THE INVENTION

The present inventors used a two hybrid system in the identification of a protein which interacts with human MITF as a target molecule. As a result, they succeeded in obtaining a protein which specifically binds to human MITF but whose functions are unclear. Further, this protein was the same as the $Cys_2/His_2$ zinc finger protein (rKr2 for "rat kruppel-type protein") derived from rat oligodendrocytes (U. Pott et al., J. Neurochem., Vol.65, No.5, 1995, 1955–1966).

When the functions of this rKr2 protein were examined, it was found that rKr2 binds to the human MITF protein via its basic domain, and thereby inhibits MITF protein binding to the promoter regions of tyrosinase and TRP1. In other words, by this process, rKr2 acts to inhibit the activation of the tyrosinase and TRP1 genes. Further, when rat rKr2 was actually introduced into human melanocytes, the expression of TRP1 was inhibited. It was thus, concluded from these results that rat rKr2 has an action to inhibit melanin synthesis.

Based on this result, the present inventors expected that a gene homologous to a rat rKr2-like gene also existed in human melanocytes, and have vigorously researched for such a gene. As a result, they finally succeeded in obtaining a gene homologous to the rat rKr2 gene, namely a cDNA encoding a protein binding to human MITF, from a human cDNA library. Thus, they succeeded first in confirming the presence of a rKr2 gene in a human being (hereinafter, also referred to as human rKr2 gene), and found that this human rKr2 gene also has melanin synthesis-inhibiting effect in a human melanocyte-culturing system.

Therefore, according to this invention, there is provided an isolated DNA comprising a gene encoding a protein which binds to and inhibits the action of a human MITF. As specific embodiments of the DNA, there can be mentioned:
1) An isolated DNA comprising a gene which is at least 85% homologous to a rat rKr2 gene and corresponds to base numbers 1843–2109 of the rat rKr2 gene,
2) An isolated DNA comprising a nucleotide sequence which hybridizes to the gene of (1) above or its complement under stringent conditions, and encodes a protein which binds to and inhibits the action of human MITF, but is not the same as the rat rKr2 gene, or
3) An isolated DNA comprising a human gene having a nucleotide sequence as set forth in SEQ ID NO:1.

When the DNA according to the present invention is, for example, integrated into a suitable expression vector and the resultant vector is introduced into melanocytes of a mammal, especially a human being, to express the DNA, the production of melanin in the melanocytes can be controlled.

Therefore, the DNA may, for example, be used for the treatment of diseases caused by abnormal melanin accumulation.

Further, the invention also provides proteins such as those containing a human rKr2 protein, which can be obtained by the expression of the DNA according to the present invention. Such proteins may be used as a tool for researches into the elucidation of the mechanism of the melanin production system in human melanocytes, or as an effective ingredient for whitening cosmetics.

As another embodiment of the invention, there is provided a method for evaluating the ability of a human melanocyte to express a protein which binds to and inhibits the action of a human MITF, using a primer prepared based on the above DNAs, particularly a DNA comprising a human gene homologous to a rat rKr2 gene or a nucleotide sequence hybridizing to the human gene above or its complement under stringent conditions and encoding a protein binding to human MITF, to inhibit the action of human MITF. According to the evaluation method, an ability of human melanocytes, particularly an ability relating to melanin production, can be evaluated. Such evaluation results may not only make the classification of melanocytes possible, but also, for example, when the results show an abnormal value, make it possible to provide a judgment criterion for taking appropriate treatment.

As another embodiment of the invention, there is provided a method for screening a substance having an influence on the expression of a protein which binds to and inhibits the action of a human MITF, in human melanocytes which comprises evaluating and screening whether or not certain substances have such an influence, using a primer prepared based on the above DNAs, particularly a DNA comprising a human gene homologous to a rat rKr2 gene, or a nucleotide sequence encoding a protein binding to human MITF, to inhibit the action of human MITF.

According to the screening method, when the pigment synthesis system of human melanocytes can be influenced by a substance so as to increase the expression of the protein, the substance can be screened as a substance inhibiting melanin deposition in human melanocytes, and, conversely, when the substance can have an influence so as to decrease the expression of the protein, the substance can be screened as a substance accelerating melanin deposition in human melanocytes. Since it can be thought that the thus screened substance can basically or primitively act on the melanin synthesis system in human melanocytes, substances of a category different from those of conventional whitening agents or tanning agents can, for example, be provided.

BRIEF DESCRIPTION OF THE DRAWINGS

FIG. 1 is a drawing showing the gene sequence of the human rKr2 fragment (SEQ ID NO:1). The upper row is human rKr2 and the lower row is rat rKr2 (SEQ ID NO:19)

FIG. 4 is a drawing showing the effect of rKr2 on binding between Mi and DNA, obtained according to a gel shift assay. Lane 1 is a negative control wherein the M box probe and the reaction solution of the in vitro transcription and translation system are mixed. Only a non-specific band shown by (a) was detected. Lane 2 is a control wherein the rKr2 protein and the probe were mixed. Likewise, only a non-specific band was detected. Lanes 3 and 7 are cases where Mi and the probe were mixed, and a specific band shown by (b) was detected. Solutions obtained by adding rKr2 to this mixed solution in increased concentrations are lanes 4 to 6. It is seen that the specific band (b) disappears. The non-specific band (a) increases in accordance with the increase of rKr2 mixing amount. Further, lanes 8 to 10 are controls wherein only the reaction solution of the in vitro transcription and translation system was mixed into the mixed solution of Mi and the probe in increased amounts.

DESCRIPTION OF THE PREFERRED EMBODIMENT

Figure 2:
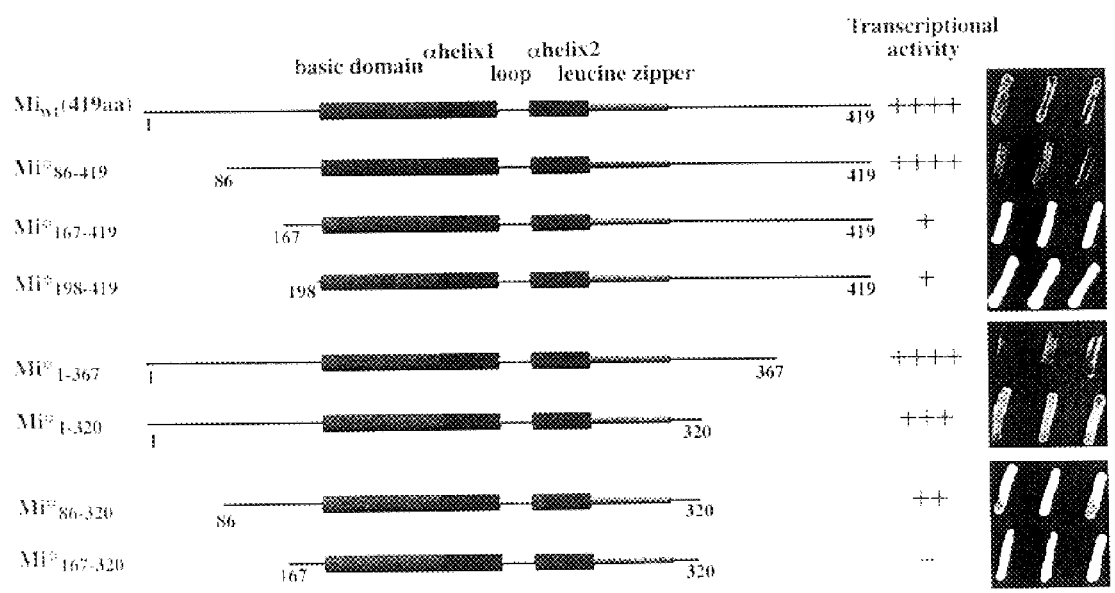
FIG. 2 is a drawing showing the transcription activities of various defective mi. The deeper the color of the yeast on the right side, the stronger is the transcription activity.

As to the protein of the invention which binds to and inhibits the action of human MITF, the binding between the protein and human MITF can be made according to any noncovalent binding mode and between any positions, but it is needed that, as a result of the binding, the action of human MITF, particularly the increase of the promoter activity of the tyrosinase gene can be inhibited. However, preferably, the protein is one that specifically binds to the E-box motif binding site of MITF.

Namely, the DNA of the invention is a gene itself encoding the above protein, or a DNA comprising the gene as a part. In the latter case, the DNA of the invention can be in the form of a suitable recombinant vector.

As specific examples of the gene, there can be mentioned a gene homologous to a rat rKr2 gene (as to its DNA sequence, see the above-mentioned U. Patt et al., J. Neurochem., Vol. 65, No. 5, 1995, 1955–1966). More specifically, the gene can be a human gene and/or comprises a nucleotide sequence which corresponds to base numbers 1843–2109 of rat rKr2 gene such as that set forth in SEQ ID NO: 1 (see FIG. 1).

The DNA of the invention also includes an isolated DNA comprising a nucleotide sequence which is a modification of the above human gene (hereinafter, also referred to as human rKr2 gene), in that the nucleotide sequence hybridizes to the human gene or its complement under stringent conditions, and encodes a protein which binds to and inhibits the action of human MITF, but is not a rat rKr2 gene. The stringent conditions mean such conditions mentioned in Sambrook J, Fritsch E F, Maniatis T: *Molecular Cloning: A Laboratory Manual*, p. 9.31–9.62, 1989, CSHL Press, (Cold Spring Harbor, N.Y.). Such conditions are well-known in the technical field that there is at least 85% homology between the two DNAs or the two DNAs do not hybridize. Modifications hybridizing to human rKr2 under such conditions include, first, one wherein one or several nucleotides in human rKr2 gene are replaced due to the degeneracy of the gene code, and, two, irrespective of the degeneracy, one wherein one or several nucleotides are replaced, and three, one wherein one or several nucleotides in human rKr2 gene are deleted or added.

However, such a modification included in the invention is limited to such that the protein encoded thereby binds to human MITF and inhibits the action of the MITF. Such a modification can be produced, for example, according to a nucleic acid synthesis process known per se, or point mutation induction or site-directed mutagenesis, based on the sequence which correspond to base numbers 1843–2109 of the rat rKr2 gene such as SEQ ID NO: 1 and/or the DNA sequence of the rat rKr2 gene.

The thus obtained human rKr2 gene or a modification thereof can be expressed in a suitable host-vector system (e.g., pQE-70, and E. coli M15 [pREP4] or SG13009 [pREP4]) to produce the protein.

In the method for evaluating the ability of a human melanocyte to express a protein which binds to and inhibits the action of a human MITF, a primer pair is used which was prepared based on a gene which is at least 85% homologous to a rat rKr2 gene and corresponds to base numbers 1843–2109 of the rat rKr2 gene, or a nucleotide sequence which hybridizes to the gene above or its complement under stringent conditions including rat or murine rKr2 gene. For example, such a primer pair can be prepared from a human rKr2 gene using endonuclease and/or exonuclease, or can be prepared according to a nucleic acid synthesis process known per se by referring to SEQ ID NO: 1. Such a primer is not limited so long as it has the chain length and sequence functional as a primer. Usually, the chain length is 12 bases or more, preferably 17 to 50 bases. Without being limited thereto, as one member of the pair of primers preferably usable in the evaluation method, there can be mentioned one prepared based on the nucleotide sequence of SEQ ID NO: 1.

As representative examples of one member of the primer pair, there can be mentioned:

5'-TCAGGGCTTAGTGCTCACCGGAGAG-3' (human sequence corresponding to 1843–1867 of rat rKr2 (hereinafter, also referred to as m-1), SEQ ID NO: 2), 5'-AGCTTTCCCACACCGGTCACATTTG-3' (human sequence corresponding to 2058–2082 of rat rKr2 (hereinafter, also referred to as m-2), SEQ ID NO: 3), 5'-GACTTGGAGCCCAGACTTCTGGCTG-3' (human sequence corresponding to 2085–2109 of rat rKr2 (hereinafter, also referred to as m-3), SEQ ID NO: 4), 5'-CCACACGGGAGAGAAACCCTATGAG-3' (human sequence corresponding to 1869–1893 of rat rKr2 (hereinafter, also referred to as m-4), SEQ ID NO: 5), and 5'-GCAAGGACTGTGGGAAAGGCTTCAG-3' (human sequence corresponding to 1895–1919 of rat rKr2 (hereinafter, also referred to as m-5), SEQ ID NO: 6).

However, the above representative members of the primer pair is in no way mentioned to further limit the present invention.

The primer pair used in the invention can be a certain combination between the above members of the primer pair, for example, the pair of m-1 and m-2, m-1 and m-3, m-4 and m-2, m-4 and m-3, m-5 and m-2, or m-5 and m-3, but can also be a combination between one of these above members and a primer prepared based on a nucleotide sequence hybridizing to human rKr2 gene under stringent conditions. As examples of such nucleotide sequence, there can be mentioned the nucleotide sequence of mouse rKr2 gene or rat rKr2 gene, and as a primer prepared based on such nucleotide sequences, there can, for example, be mentioned 5'-CCCCAGTGTGAATTCTCTTATG-3' (the sequence of mouse corresponding to 2110–2231 of rat rKr2 (hereinafter, also referred to as m-6), SEQ ID NO: 7).

As preferred examples of primer pairs containing primer m-6 as one member, there can be mentioned pairs of m-1 and m-6, m-4 and m-6, and m-5 and m-6.

The nucleotide sequences of the above specific primer pairs are shown as follows.

P-1: 5'-TCAGGGCTTAGTGCTCACCGGAGAG-3' (SEQ ID NO: 2), (m-1) and
5'-AGCTTTCCCACACCGGTCACATTTG-3' (SEQ ID NO: 3), (m-2);

P-2: 5'-TCAGGGCTTAGTGCTCACCGGAGAG-3' (SEQ ID NO: 2), (m-1) and
5'-GACTTGGAGCCCAGACTTCTGGCTG-3' (SEQ ID NO: 4), (m-3);

P-3: 5'-TCAGGGCTTAGTGCTCACCGGAGAG-3' (SEQ ID NO: 2), (m-1) and
5'-CCCCAGTGTGAATTCTCTTATG-3' (SEQ ID NO: 7), (m-6)

P-4: 5'-CCACACGGGAGAGAAACCCTATGAG-3' (SEQ ID NO: 5), (m-4) and
5'-AGCTTTCCCACACCGGTCACATTTG-3' (SEQ ID NO: 3), (m-2);

P-5: 5'-CCACACGGGAGAGAAACCCTATGAG-3' (SEQ ID NO: 5), (m-4) and
5'-GACTTGGAGCCCAGACTTCTGGCTG-3' (SEQ ID NO: 4), (m-3);

P-6: 5'-CCACACGGGAGAGAAACCCTATGAG-3' (SEQ ID NO: 5), (m-4) and
5'-CCCCAGTGTGAATTCTCTTATG-3' (SEQ ID NO: 7), (m-6);

P-7: 5'-GCAAGGACTGTGGGAAAGGCTTCAG-3' (SEQ ID NO: 6), (m-5) and
5'-AGCTTTCCCACACCGGTCACATTTG-3' (SEQ ID NO: 3), (m-2);

P-8: 5'-GCAAGGACTGTGGGAAAGGCTTCAG-3' (SEQ ID NO: 6), (m-5) and
5'-GACTTGGAGCCCAGACTTCTGGCTG-3' (SEQ ID NO: 4), (m-3); and P-9: 5'-GCAAGGACTGTGGGAAAGGCTTCAG-3' (SEQ ID NO: 6), (m-5) and
5'-CCCCAGTGTGAATTCTCTTATG-3' (SEQ ID NO: 7), (m-6).

In the above evaluation method, mRNAs or total RNAs, particularly mRNAs, are extracted from human melanocytes. According to a conventional method, the mRNAs obtained are converted to cDNAs with reverse transcriptase, and then so-called Reverse Transcription-Polymerase Chain Reaction (hereinafter "RT-PCR") is carried out wherein, using the cDNAs obtained as a template and using the primer, the elongation of the DNA chain is repeated. PCR operation conditions are well-known by a person skilled in the art, for example, such as those conditions taught by Sambrook J. Fritsch E F, Maniatis T: Molecular Cloning: A Laboratory Manual, CSHL Press, Cold Spring Harbor, N.Y., P14.2 (1989). More specifically, those conditions comprising 95° C., 1 minute denaturation, 40 reaction cycles (95° C., 30 seconds and 68° C., 4 minutes), and 72° C., 10 minutes annealing. Enzymes and other reagents, and further apparatuses used in the PCR can be commercially available ones, and the operations can be carried out according to the operating manual of the distributor.

The amount of the thus obtained RT-PCR product has a correlation with the ability of human melanocytes to express the human rKr2 gene. Therefore, the expression ability of human melanocytes of the human rKr2 gene can be evaluated by hybridizing the RT-PCR product obtained under certain conditions to the human rKr2 gene, preferably under stringent conditions, and detecting the degree of the hybridization, for example, the presence or absence of the DNA hybridizing thereto (namely, confirmation of the presence or absence of human rKr2 gene) or the amount of the DNA hybridizing thereto.

As an alternative method, the evaluation of the ability of human melanocytes to express the protein inhibiting the action of human MITF can also be made, for example, by hybridization using a probe of the target gene, and Northern blotting and Western blotting. Thus, as mentioned above, the degree of hybridization has a correlation with the expression ability of human melanocytes of the human rKr2 gene. Therefore, finally, according to the evaluation method of the present invention, the fundamental production ability of melanin pigments in melanocytes can be evaluated. As a specific embodiment of this evaluation system, there can be mentioned the following:

A method for evaluating the ability of a human melanocyte to express a protein which binds to and inhibits the action of a human MITF, which comprises:
(A) preparing a primer pair from (1) a gene which is at least 85% homologous to a rat rKr2 gene and corresponds to base numbers 1843–2109 of the rat rKr2 gene, or (2) a nucleotide sequence which hybridizes to the gene of (1) or its complement under stringent conditions, and encodes a protein which binds to and inhibits the action of the human MITF,
(B) performing a RT-PCR on mRNAs or total RNAs extracted from the human melanocyte, using the primer pair, to obtain a RT-PCR product,
(C) hybridizing the RT-PCR product to a human rKr2 gene to detect the amount of the RT-PCR product, and
(D) evaluating, based on the amount of the RT-PCR product, the ability of the human melanocyte to express the protein which binds to and inhibits the action of human MITF.

When, in the above evaluation system, after the human melanocytes as an evaluation target are cultured in the presence and absence of a certain substance, the expression abilities of human melanocytes of the protein inhibiting the action of the human MITF in the melanocytes obtained are mutually compared, and an evaluation can be made on the influence of the substance on the production of melanin pigments in the melanocytes. Therefore, by this method, it can be evaluated whether a certain substance can inhibit or accelerate the pigment production of human melanocytes, and thus, the screening of a novel whitening agent or tanning agent is made possible.

Culturing of the human melanocytes can be carried out according. to a conventional method, and the substance can be made to exist in the culture system at a suitable concentration.

The DNA comprising a human rKr2 gene, according to the invention, will, for example, be usable not only for tests or researches for solving the mechanism of the pigment formation system in melanocytes, but also for the treatment of melanocytes having an abnormality in melanin production. Further, fragments of the gene can be used as primers of PCR having various purposes.

The invention is further specifically described according to following specific examples. However, the examples recited does not further limit the scope of the present invention.

EXAMPLE 1

Obtaining the MITF-bound Protein

MITF (hereinafter, also referred to as Mi)-bound protein was obtained from a rat heart library using an yeast two hybrid system. The yeast used was EGY 48 MAT, a trp1 ura3 his3 LEU2::pLexAop6-LEU2 yeast. pJK103 into which lacZ gene was integrated was used as the reporter plasmid. Further, pL202 into which LexA was integrated was used as a plasmid for bait, and pJG4–5 was used as a library plasmid.

First, a bait of Mi was prepared before screening. Since Mi itself is a transcription factor, has transcription activity and disturbs the detection system, an operation to remove this active region from Mi was made. As shown in FIG. 2, various mutants wherein Mi was deleted were prepared, and checked for transcription performance. The stronger the blue color, the higher the transcription activity is. As a result, in Mi wherein both of the N-terminus and the C-terminus were deleted, shown by Mi*167–320, the transcription activity disappeared. Thus, this Mi*167–320 (hereinafter, referred to as Mi*) which includes the b-HLH-zip domain, was used for screening.

$10^6$ transformed yeasts wherein the rat heart library was introduced were screened using Mi* bait. The screening was carried out according to Wang, et al., Science 256, 674–676, 1994. 85 yeast clones showing positiveness in a leucine-auxotrophic selective medium were subjected to color change selection with X-gal to result in 17 clones. When examination was carried out on 14 clones among them, whose plasmid could be recovered, they had the same gene, a known rKr2 gene. This gene encodes a zinc finger-type protein and was previously obtained from oligodendrocyte cells, but its functions were unknown.

EXAMPLE 2

Binding Specificity of rKr2 to Human MITF

Figure 3:
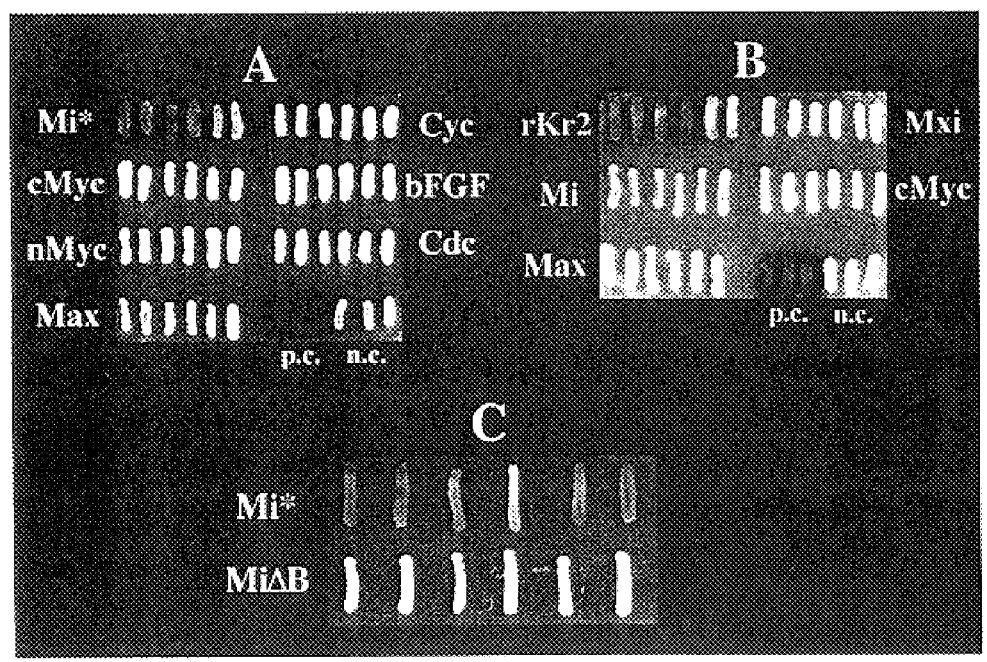
FIG. 3 is a drawing showing the specificity of. binding between rKr2 and Mi, and binding between the basic region of defective Mi and rKr2. Panel A shows binding between rKr2 and various proteins containing Mi, and Panel B shows binding between Mi and various proteins containing rKr2. Panel C shows binding between Mi from which the basic region was removed (MiDB) and rKr2.

Binding specificity of this rKr2 to human MITF (in the examples, hereinafter, referred to as Mi) was examined. Panels A and B in FIG. 3 are the results.

Yeasts wherein rKr2 was introduced are shown in Panel A, and into the yeasts are introduced genes encoding proteins (cMyc, nMyc and Max) having a structure similar to Mi* and Mi (bHLH-Zip) and genes encoding other proteins, respectively. rKr2 specifically binds only to Mi, and makes the color of the yeast blue. In Panel B, conversely, genes encoding various proteins were introduced into yeasts wherein Mi was introduced, and it was clarified that Mi also specifically binds only to rKr2.

EXAMPLE 3

Site of Mi to Which rKr2 Binds

The site of Mi to which rKr2 binds was found out. MiDB shown in Panel C in FIG. 3 is a protein obtained by deleting 5 amino acids (Glu212 Arg Arg Arg Arg216) in the basic region of Mi.

The preparation of the mutant was carried out as follows. First, the following primer pairs (1) and (2) were used, and PCR was carried out on the full length of Mi using each pair to give products.
(1)
   5-AACTCGAATTCATGCTGGAAATGCTAGAATAT-3
   (SEQ ID NO: 8)
   (EcoRI site+nt1–12) and
   5-TTTATGTTAAAAATCAGGTTGTGATTGTCC-3
      (SEQ ID NO: 9)
   (nt(618–636)+(652–662)),
(2) 5-CAACCTGATTTTTAACATAAATGACCGCAT-3
   (SEQ ID NO: 10)

(nt(627–636)+(652–671)) and

5-TCACGTCGACCTAACAAGTGTGCTCCGTC-3 (SEQ ID NO: 11)

(sa11 site+nt1242–1260)

The two PCR products prepared were mixed as templates, and the third PCR was carried out using the following primer pair.

(3) 5-GATCGGAATTCGGCCTCACCATCAGCAAC-3 (SEQ ID NO: 12)

(EcoRI site+nt499–516) and

5-TCACGTCGACAACGGGTTCTTGCTTGATG-3 (SEQ ID NO: 13)

(sa11 site+nt942–960)

The PCR product was cloned into PL202 vector, and it was confirmed that the defective product was produced.

When binding between this defective Mi (MiDB) and rKr2 gene was examined, it was found that the binding strikingly lowers as shown in Panel C in FIG. 3. Namely, it is seen that the amino acids in the basic region are important for binding between rKr2 and Mi.

EXAMPLE 4

Gel Shift Assay

Further, the influence of rKr2 on Mi was examined by gel shift assay. Gel shift assay was carried out according to the method of Zervos, et al., Cell 72, 223–232, 1993. Mi and rKr2 protein were prepared using an in vitro transcription and translation system (made. by Promega Corporation). The end of a double-strand oligonucleotide

5-AAAGTCAGTCATGTGCTTTTCAGAGGATGA-3 (SEQ ID NO: 14), which is a DNA motif which exists in the promoters of tyrosinase and TRP1 and to which Mi binds, was [g-32p] labeled, and purified from a gel, and the resultant product was used as a probe. First, Mi and rKr2 protein were mixed in a binding buffer (10 mM Tris (pH 7.4), 80 mM, NaCl, 1 mM DTT, 5% glycerol, single-strand oligonucleotide as a non-specific competitor), and subjected to reaction at room temperature for 10 minutes. Then, the oligonucleotide probe prepared was added, and reaction was carried out at room temperature for 20 minutes. The reaction mixture was electrophroresed using 0.5×TBE buffer and acrylamide gel containing 0.01% NP-40.

The results are shown in FIG. 4. Mi binds to the probe to form a complexed pair, which is detected as a specific band. When rKr2 protein was added thereto, it could be observed that this specific band decreased depending on the concentration of rKr2 protein. Namely, it is seen that rKr2 protein has an action to inhibit the binding of Mi to the DNA.

EXAMPLE 5

Examination of Melanin Synthesis-controlling Action

For examining what action rKr2 has on melanin synthesis control, rKr2 was introduced into human normal melanocytes. Human normal melanocytes (made by Cascade Biologics Inc.) were grown on a coverslip, and rKr2 having an HA epitope tag, integrated into pMT3 vector, was injected into the melanocytes by an automatic micro-injection system (Pepperkok, et al., J. Biol. Chem., 269, 6986–6991, 1995). As a control, pMT3 wherein no insert was inserted was injected, together with a rabbit marker antibody, into human normal melanocytes, and the resultant melanocytes were used as a control. After 24 hours, the melanocytes of each group were fixed with 4% paraformaldehyde, and stained with an anti-HA rabbit polyclonal antibody (made by Santa Cruz Biotechnology Inc.), an anti-rabbit antibody to which biotin was bound and streptavidin-texas red. Further, at the same time, the same melanocytes were stained with an anti-TRP1 mouse monoclonal antibody (Chemicon International Inc.) and an anti-mouse FITC antibody. The results from the observation of the resultant melanocytes by a laser confocal microscope are shown in FIG. 5.

The melanocytes wherein rKr2 was introduced and expressed are stained red. It is seen that since rKr2 is a transcription factor, it is expressed in the nucleus. On the other hand, the expression of TRP1 is shown by a green stain, and it is seen that the melanocytes express TRP1 in the ordinary state. From the expression amount of TRP1 (arrows in Panels B and F in FIG. 5) in the melanocytes wherein rKr2 was expressed, it is seen that the expression thereof disappeared. Namely, it was found that the expression of TRP1 gene in the melanocytes was inhibited by the expression of rKr2.

From the above results, rKr2 binds to the DNA binding region of Mi and inhibits Mi from binding to the promoter of tyrosinase or TRP1. From this, it was concluded that the expression of the melanin synthesis gene is suppressed and melanin synthesis is inhibited.

EXAMPLE 6

Obtaining the Human rKr2-homologous Gene

For obtaining a human rKr2 homolog, the following various primers were prepared from the sequence of rat rKr2, and PCR was carried out using a human fetal brain cDNA (obtained from STRATEGENE) template.

Primers used for the First PCR

MR516R 5'-CTCAGGGCTTAGTGCTCACCGG (SEQ ID NO: 15)

(corresponding base numbers in rat rKr2=nt1843–1867) and

T3 universal primer 5'-ATTAACCCTCACTAAAGGGA (SEQ ID NO: 16)

Primers used for the Second PCR

MR446R 5'-CATAAGAGAATTCACACTGGGG (SEQ ID NO: 17)

(corresponding base numbers in rat rKr2=nt2178–2199)

SK universal primer 5'-GCCGCTCTAGAACTAGTGGATC (SEQ ID NO: 18)

The band obtained in the second PCR was cloned and subjected to sequence analysis to give a sequence shown in FIG. 1. This sequence has 89% homology to the sequence of base numbers 1843 to 2109 of rat rKr2. This sequence was also compared with sequences obtained in gene data bases on homology, and it was found that rKr2 is a gene having the highest homology, and thus the sequence was judged to be a fragment of the human rKr2 homolog gene.

EXAMPLE 7

Confirmation of the Expression of Human rKr2 Gene in Human Melanocytes

A partial sequence of the obtained human rKr2 homolog gene is shown in FIG. 1. The expression of the human rKr2 homolog in human melanocytes was examined according to an RT-PCR method using the following primers prepared based on this human sequence.

5'-TCAGGGCTTAGTGCTCACCGGAGAG-3' (SEQ ID NO: 2)
(corresponding base numbers in rat rKr2=nt1843–1867)

5'-GACTTGGAGCCCAGACTTCTGGCTG-3' (SEQ ID NO: 4)
(corresponding base numbers in rat rKr2=nt2085–2109)

mRNAs or total RNAs of human normal melanocytes were extracted, cDNAs were synthesized therefrom using a reverse transcriptase, and PCR was carried out using the cDNAs as a template and the above primers. The resultant band was cloned and sequenced for the nucleotide sequence to confirm that the band was rKr2.

EXAMPLE 8
Confirmation of the Expression of Human rKr2 Gene in Human Melanocytes The operations of Example 7 were repeated except that the primer air consisting of SEQ ID NO: 2 and SEQ ID NO: 7 was used in place of the primer pair consisting of SEQ ID NO: 2 and SEQ ID NO: 4, and as a result, the same result as in Example 7 was confirmed.

EXAMPLE 9
Examination of Melanin Synthesis Control

Figure 5:
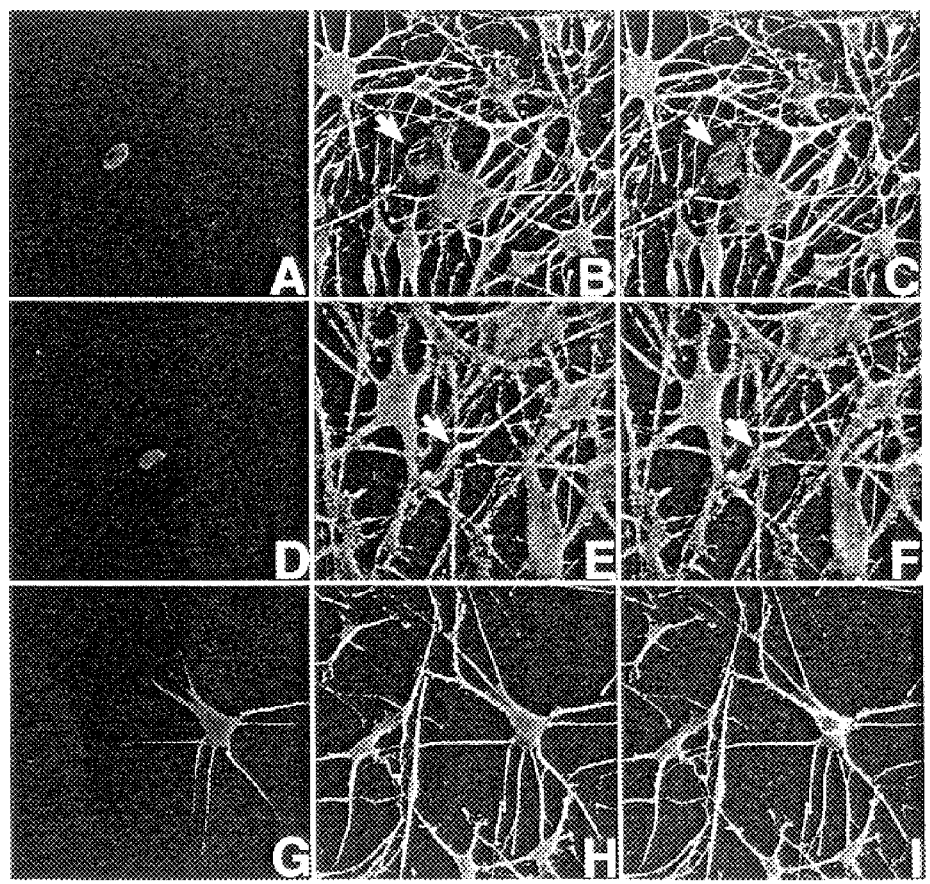
FIG. 5 is a drawing wherein rKr2 is injected into human melanocytes, and the expression of rKr2 is shown in red and the expression of TRP1 in green. Panels A and D show melanocytes expressed in the nucleus. Panels B, E and H show the expression of TRP1. Panels. C, F and I are superimposed images of A and B, D and E, and G and H, respectively. In the melanocytes shown by the arrow, rKr2 is expressed. It is seen that the TRP1 expression in the melanocytes disappeared.

For examining the action of the above human rKr2 fragment on pigment synthesis control, the human rKr2 fragment was introduced into human normal melanocytes in the same manner as in Example 5. As a result, the same result as in FIG. 5 was obtained. Namely, it was confirmed that the expression of the TRP1 gene in human melanocytes was inhibited by the expression of the human rKr2 fragment.

What is claimed is:

1. An isolated polynucleotide consisting of a human DNA fragment encoding a protein which binds to and inhibits the action of a human microphthalmia-associated transcription factor (MITF), said DNA fragment consisting of:
   (a) the nucleotide sequence as set forth in SEQ ID NO: 1, or
   (b) a nucleotide sequence which (i) is greater than 89% homologous to the nucleotide sequence of (a) or its complement and (ii) consists of at most 267 nucleotides.

2. An isolated protein obtained by an expression of the polynucleotide according to claim 1.

3. A method for evaluating the ability of a human melanocyte to express a protein which binds to and inhibits the action of a human MITF, which comprises:
   (A) preparing a primer pair from a DNA fragment consisting of
      (a) the nucleotide sequence as set forth in SEQ ID NO: 1, or
      (b) a nucleotide sequence which (i) is greater than 89% homologous to the nucleotide sequence of (a) or its complement and (ii) consists of at most 267 nucleotides,
   (B) performing a Reverse Transcription-Polymerase Chain Reaction (hereinafter "RT-PCR") on mRNAs or total RNAs extracted from the human melanocyte, using the primer pair, to obtain a RT-PCR product,
   (C) hybridizing the RT-PCR product to a human DNA fragment encoding a protein which binds to and inhibits the action of the human MITF, to detect the amount of the RT-PCR product, and
   (D) evaluating, based on the amount of the RT-PCR product, the ability of the human melanocyte to express the protein which binds to and inhibits the action of human MITF.

4. The method according to claim 3, wherein one member of the primer pair in step (A) is selected from the group of primers consisting of SEQ ID NOs: 2–6.

5. The method according to claim 3, wherein the primer pair in step (A) is selected from the group consisting of the following primer pairs P-1 to P-9:

P-1: SEQ ID NOs: 2 and 3,
P-2: SEQ ID NOs: 2 and 4,
P-3: SEQ ID NOs: 2 and 7,
P-4: SEQ ID NOs: 5 and 3,
P-5: SEQ ID NOs: 5 and 4,
P-6: SEQ ID NOs: 5 and 7,
P-7: SEQ ID NOs: 6 and 3, P-8: SEQ ID NOs: 6 and 4, and P-9: SEQ ID NOs: 6 and 7.

6. The method according to claim 3, wherein the DNA fragment of step (A) is a human DNA fragment.

7. An isolated polynucleotide consisting of a human DNA fragment encoding a protein which binds to and inhibits the action of a human microphthalmia-associated transcription factor (MITF), said DNA fragment consisting of the nucleotide sequence as set forth in SEQ ID NO; 1.

8. An isolated protein obtained by an expression of the polynucleotide according to claim 7.

9. A method for evaluating the ability of a human melanocyte to express a protein which binds to and inhibits the action of a human MITF, which comprises:

(A) preparing a primer pair from a DNA fragment consisting of the nucleotide sequence as set forth in SEQ ID NO: 1, (B) performing a Reverse Transcription-Polymerase Chain Reaction (hereinafter "RT-PCR") on mRNAs or total RNAs extracted from the human melanocyte, using the primer pair, to obtain a RT-PCR product, (C) hybridizing the RT-PCR product to a human DNA fragment encoding a protein which binds to and inhibits the action of the human MITF, to detect the amount of the RT-PCR product, and (D) evaluating, based on the amount of the RT-PCR product, the ability of the human melanocyte to express the protein which binds to and inhibits the action of human MITF.

10. The method according to claim 9, wherein one member of the primer pair in step (A) is selected from the group of primers consisting of SEQ ID NOs: 2–6.

11. The method according to claim 9, wherein the primer pair in step (A) is selected from the group consisting of the following primer pairs P-1 to P-9:

P-1: SEQ ID NOs: 2 and 3,

P-2: SEQ ID NOs: 2 and 4,

P-3: SEQ ID NOs: 2 and 7,

P-4: SEQ ID NOs: 5 and 3,

P-5: SEQ ID NOs: 5 and 4,

P-6: SEQ ID NOs: 5 and 7,

P-7: SEQ ID NOs: 6 and 3,

P-8: SEQ ID NOs: 6 and 4, and

P-9: SEQ ID NOs: 6 and 7.

12. The method according to claim 9, wherein the DNA fragment of step (A) is a human DNA fragment.

13. The method according to claim 7, wherein one member of the primer pair in step (A) is prepared from the DNA fragment consisting of the nucleotide sequence which (i) is greater than 89% homologous to the nucleotide sequence of (a) or its complement and (ii) consists of at most 267 nucleotides.

14. The method according to claim 3, wherein one member of the primer pair in step (A) is prepared from the DNA fragment consisting of the nucleotide sequence of SEQ ID NO: 1.

15. The method according to claim 3, wherein the DNA fragment of step (A) consists of the nucleotide sequence of SEQ ID NO: 1.

\* \* \* \* \*

SEQUENCE LISTING

<160> NUMBER OF SEQ ID NOS: 19

<210> SEQ ID NO 1
<211> LENGTH: 267
<212> TYPE: DNA
<213> ORGANISM: Homo sapiens

<400> SEQUENCE: 1
tcagggctta gtgctcaccg gagagtccac acgggagaga aaccctatga g tgcaaggac    60 tgtgggaaag gcttcagtct tgcctcaagt ctacggactc atcagagagt t cacactggt   120 gagaagccct tccaatgcaa tgagtgccag aagcggttca gtcaggtctc a cacctccag   180 tcccaccaga gagtgcacac tggggagaag ccctacaaat gtgaccggtg t gggaaagct   240 ttcagccaga agtctgggct ccaagtc                                        267

<210> SEQ ID NO 2
<211> LENGTH: 25
<212> TYPE: DNA
<213> ORGANISM: Artificial Sequence
<220> FEATURE:
<223> OTHER INFORMATION: Description of Artificial  Sequence: "Synthetic
      DNA"

<400> SEQUENCE: 2
tcagggctta gtgctcaccg gagag                                           25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial  Sequence: "Synthetic
      DNA"

<400> SEQUENCE: 3
agctttccca caccggtcac atttg                                           25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial  Sequence: "Synthetic
      DNA"

-continued

```
<400> SEQUENCE: 4
gacttggagc ccagacttct ggctg                                          25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial  Sequence: "Synthetic
      DNA"

<400> SEQUENCE: 5
ccacacggga gagaaaccct atgag                                          25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial  Sequence: "Synthetic
      DNA"

<400> SEQUENCE: 6
gcaaggactg tgggaaaggc ttcag                                          25

<210> SEQ ID NO 7
<211> LENGTH: 22
<212> TYPE: DNA
<213> ORGANISM: Artificial Sequence
<220> FEATURE:
<223> OTHER INFORMATION: Description of Artificial  Sequence: "Synthetic
      DNA"

<400> SEQUENCE: 7
ccccagtgtg aattctctta tg                                             22

<210> SEQ ID NO 8
<211> LENGTH: 32
<212> TYPE: DNA
<213> ORGANISM: Artificial Sequence
<220> FEATURE:
<223> OTHER INFORMATION: Description of Artificial  Sequence: "Synthetic
      DNA"

<400> SEQUENCE: 8
aactcgaatt catgctggaa atgctagaat at                                  32

<210> SEQ ID NO 9
<211> LENGTH: 30
<212> TYPE: DNA
<213> ORGANISM: Artificial Sequence
<220> FEATURE:
<223> OTHER INFORMATION: Description of Artificial  Sequence: "Synthetic
      DNA"

<400> SEQUENCE: 9
tttatgttaa aaatcaggtt gtgattgtcc                                     30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial  Sequence: "Synthetic
      DNA"

<400> SEQUENCE: 10
```
caacctgatt tttaacataa atgaccgcat                               30

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: "Synthetic
      DNA"

<400> SEQUENCE: 11
tcacgtcgac ctaacaagtg tgctccgtc                                29

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: "Synthetic
      DNA"

<400> SEQUENCE: 12
gatcggaatt cggcctcacc atcagcaac                                29

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: "Synthetic
      DNA"

<400> SEQUENCE: 13
tcacgtcgac aacgggttct tgcttgatg                                29

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: "Synthetic
      DNA"

<400> SEQUENCE: 14
aaagtcagtc atgtgctttt cagaggatga                               30

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: "Synthetic
      DNA"

<400> SEQUENCE: 15
ctcagggctt agtgctcacc gg                                       22

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: "Synthetic
      DNA"

<400> SEQUENCE: 16

```
attaaccctc actaaaggga                                                    20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial  Sequence: "Synthetic
      DNA"

<400> SEQUENCE: 17
cataagagaa ttcacactgg gg                                                 22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial  Sequence: "Synthetic
      DNA"

<400> SEQUENCE: 18
gccgctctag aactagtgga tc                                                 22

<210> SEQ ID NO 19
<211> LENGTH: 269
<212> TYPE: DNA
<213> ORGANISM: Rat Oligodendrocytes

<400> SEQUENCE: 19
attcagggct tactgctcac cggagggtcc acacgggaga gaagccctat g aatgcacag       60 agtgtgggaa aggctttagt cttgcctcaa gtctacgaac tcatcagcga a ttcacaccg      120 gcgagaaacc cttccaatgc aatgagtgcc agaagaggtt cagtcaggtc t cacacctcc     180 agtcccacca gagggttcac acaggggaga agccttacaa atgtgacacc t gtgggaagg    240 ccttcagtca aaagtctggt ctccaagtc                                        269
```